(12) United States Patent
Contreras

(10) Patent No.: US 10,370,578 B2
(45) Date of Patent: Aug. 6, 2019

(54) METHOD OF ENCAPSULATING SIGNALING AGENTS FOR USE DOWNHOLE

(71) Applicant: Saudi Arabian Oil Company, Dhahran (SA)

(72) Inventor: Elizabeth Q. Contreras, Houston, TX (US)

(73) Assignee: Saudi Arabian Oil Company (SA)

( * ) Notice: Subject to any disclaimer, the term of this patent is extended or adjusted under 35 U.S.C. 154(b) by 0 days.

(21) Appl. No.: 15/914,083

(22) Filed: Mar. 7, 2018

(65) Prior Publication Data

US 2018/0258337 A1    Sep. 13, 2018

Related U.S. Application Data

(60) Provisional application No. 62/468,076, filed on Mar. 7, 2017.

(51) Int. Cl.
  *E21B 33/14*     (2006.01)
  *E21B 47/00*     (2012.01)
  (Continued)

(52) U.S. Cl.
  CPC ............ *C09K 8/467* (2013.01); *B01J 13/16* (2013.01); *C04B 20/1033* (2013.01);
  (Continued)

(58) Field of Classification Search
  CPC ... E21B 33/14; E21B 47/005; C04B 2103/54; C04B 28/02; C04B 40/0096;
  (Continued)

(56) References Cited

U.S. PATENT DOCUMENTS

| 3,429,827 A | 2/1969 | Ruus |
| 6,527,051 B1 | 3/2003 | Reddy et al. |

(Continued)

FOREIGN PATENT DOCUMENTS

| WO | WO2014189766 A2 | 11/2014 | |
| WO | WO-2016057027 A1 * | 4/2016 | ............... C09K 8/44 |

(Continued)

OTHER PUBLICATIONS

E. Quevedo et al., Interfacial Polymerization Within a Simplified Microfuidic Device: Capturing Capsules. J. AM CHEM. SOC. 2005, 127, 10498-10499.

(Continued)

*Primary Examiner* — Daniel P Stephenson
(74) *Attorney, Agent, or Firm* — Bracewell LLP; Constance G. Rhebergen

(57) ABSTRACT

A method of monitoring conditions in a wellbore by disposing capsules with a signaling agent downhole, and monitoring the presence of the signaling agent released from the capsules that escape the wellbore. The capsules are formed by combining immiscible liquids, where one of the liquids contains the signaling substance, and each of the liquids contains a reagent. When combined, the liquids segregate into a dispersed phase and a continuous phase, with the dispersed phase having the signaling agent. The reagents react at the interfaces between dispersed and continuous phases and form polymer layers encapsulating the signaling agent to form the capsules. When disposed downhole, such as in casing cement, the capsule membranes can burst under pressure or temperature to release the signaling agent. Adjusting relative concentrations of the reagents varies membrane strength and permeability.

20 Claims, 4 Drawing Sheets

(51) Int. Cl.
*B01J 13/16* (2006.01)
*C04B 24/24* (2006.01)
*C09K 8/467* (2006.01)
*G01N 33/38* (2006.01)
*C04B 28/02* (2006.01)
*C04B 20/10* (2006.01)
*C04B 103/00* (2006.01)
*C04B 103/54* (2006.01)
*C04B 111/80* (2006.01)

(52) U.S. Cl.
CPC .............. *C04B 24/24* (2013.01); *C04B 28/02* (2013.01); *E21B 33/14* (2013.01); *E21B 47/0005* (2013.01); *G01N 33/383* (2013.01); *C04B 2103/0058* (2013.01); *C04B 2103/0062* (2013.01); *C04B 2103/54* (2013.01); *C04B 2111/80* (2013.01); *C04B 2111/807* (2013.01)

(58) Field of Classification Search
CPC . C04B 20/1033; C04B 22/00; C04B 40/0633; C04B 40/0641; C04B 2103/0058; C04B 2103/0062; C04B 2111/80; C04B 2111/807; C04B 24/24; B01L 13/16; C09K 8/467; G01N 33/383
See application file for complete search history.

(56) References Cited

U.S. PATENT DOCUMENTS

| | | | |
|---|---|---|---|
| 6,554,071 B1 | 4/2003 | Reddy et al. | |
| 7,712,527 B2 | 5/2010 | Roddy | |
| 8,047,282 B2* | 11/2011 | Lewis | C09K 8/467 166/177.1 |
| 8,506,907 B2 | 8/2013 | Angelescu | |
| 8,877,506 B2 | 11/2014 | Roberts et al. | |
| 9,410,076 B2* | 8/2016 | Reddy | C09K 8/035 |
| 9,494,032 B2 | 11/2016 | Roberson | |
| 9,505,659 B2* | 11/2016 | Bickbau | C04B 7/527 |
| 9,856,414 B2* | 1/2018 | Sundaram | C09K 8/805 |
| 2004/0171499 A1 | 9/2004 | Ravi et al. | |
| 2006/0102345 A1 | 5/2006 | McCarthy et al. | |
| 2013/0062068 A1 | 3/2013 | Roddy et al. | |
| 2013/0126164 A1* | 5/2013 | Sweatman | E21B 21/003 166/282 |
| 2015/0034310 A1 | 2/2015 | Brennecke et al. | |
| 2015/0101810 A1* | 4/2015 | Aines | C04B 28/02 166/292 |
| 2015/0344376 A1 | 12/2015 | Bowers et al. | |
| 2016/0040524 A1 | 2/2016 | Ravi et al. | |
| 2016/0177698 A1 | 6/2016 | Schultheiss et al. | |
| 2016/0281498 A1 | 9/2016 | Nguyen et al. | |
| 2017/0296440 A1* | 10/2017 | Gross | A61K 31/14 |
| 2018/0079947 A1* | 3/2018 | Contreras | C04B 14/465 |
| 2018/0258337 A1* | 9/2018 | Contreras | C04B 28/02 |

FOREIGN PATENT DOCUMENTS

| | | | | |
|---|---|---|---|---|
| WO | WO-2016068951 A1 * | 5/2016 | ............ | C09K 8/805 |
| WO | WO2016068951 A1 | 5/2016 | | |
| WO | WO-2017137789 A1 * | 8/2017 | .......... | C04B 22/008 |

OTHER PUBLICATIONS

J. Steinbacher et al., "Polymer Chemistry in Flow: New Polymers, Beads, Capsules, and Fibers." Journal of Polymer Science: Part A: Polymer Chemistry, vol. 44, 6505-6533 (2006).

S. Broadwater et al., One-Pot Multi-Step Synthesis: A Challenge Spawning Innovation. ORG. BIOMOL. CHEM., 2005, 3, 2899-2906.

T. Tadros. Polymeric Surfactants in Disperse Systems. Advances in Colloid and Interface Science 147-148 (2009) 281-299.

International Search Report and Written Opinion dated May 16, 2018 of related application PCT/US2018/021291.

* cited by examiner

METHOD OF ENCAPSULATING SIGNALING AGENTS FOR USE DOWNHOLE

CROSS-REFERENCE TO RELATED APPLICATION

This application claims priority from U.S. Provisional Application Ser. No. 62/468,076 filed Mar. 7, 2017, the full disclosure of which is incorporated by reference in its entirety and for all purposes.

BACKGROUND

1. Field

The present disclosure relates to encapsulating a signaling agent for use downhole, and monitoring releases of the signaling agent. More specifically, the present disclosure relates to forming a membrane that encapsulates the signaling agent and that releases the signaling agent under designated conditions.

2. Description of Prior Art

Hydrocarbons that are produced from subterranean formations typically flow from the formation to surface via wellbores that are drilled from surface and intersect the formation, where the wellbores are often lined with tubular casing. The casing is usually bonded to the inner surface of the wellbore with a cement that is injected into an annulus that is between the casing and wellbore. In addition to anchoring the casing within the wellbore, the cement also isolates adjacent zones within the formation from one another. Without the cement isolating these adjacent zones, the different fluids could become mixed, which requires subsequent separation, or can reduce the hydrocarbon producing potential of the wellbore.

The cement also blocks hydrocarbon fluid flow in the annulus between the casing and the wellbore wall. Without the cement, or in instances when cement has failed, hydrocarbon from the formation is known to migrate to surface. Sensors are available for monitoring cement integrity; but are brittle and thus subject to fracture when exposed to vibration and high temperatures downhole. Acoustic interrogation in the wellbore is another currently known technique for assessing cement quality, where a downhole tool is deployed within the casing which emits or induces sonic waves within the cement. Reflected waves are formed when the waves reach interfaces in the cement, and which are monitored and analyzed for cement evaluation. Acoustic monitoring though is time consuming and is performed when the well is off-line and not producing.

SUMMARY

Disclosed is an example of a method of wellbore operations and which includes providing a first fluid having a signaling agent and a first reagent, providing a second fluid that is immiscible with the first fluid and that contains a second reagent that is combinable with the first reagent to form a polymer, combining the first and second fluids so that the first fluid is dispersed in the second fluid to form vesicles of the first fluid in the second fluid, and so that the first and second reagents react at interfaces between the first and second fluids to form polymer layers that encapsulate the vesicles, and which form capsules containing the signaling agent, controlling a characteristic of the polymer layers by adjusting a concentration of a one of the first and second reagents, disposing the capsules in a wellbore, and monitoring for the presence of signaling agents that escape from the capsules. The capsules are optionally disposed in cement in the wellbore. The method optionally includes monitoring the concentration of the signaling agent that releases from the capsules. In this example, the signaling agent is a first signaling agent, and the method alternatively further includes forming capsules having a second signaling agent and disposing the capsules having the second signaling agent at a designated depth in the wellbore that is different from a depth where capsules having the first signaling agent are disposed in the wellbore. A characteristic of the cement is identifiable based on the step of monitoring the signaling agent. Examples materials of the signaling agent include a dye, a fluorophore, an isotope, and combinations thereof. The first and second reagents are alternatively compounds having a reactive functional group, and include one or more of monomers with tri-functional acid chlorides and monomers with di-functional amino groups. The method further optionally includes encapsulating a sealing reagent for sealing cement. Example characteristics of the polymer layers include permeability and yield strength. In example embodiments, the polymer layers are formulated to fail at one of a designated pressure, a designated temperature, or a designated temperature and designated pressure. In an embodiment, the method further includes controlling a release rate of the signaling agent from the polymer layers by adjusting one or more of, a viscosity of the first fluid, a permeability of the polymer layers, a size of the reagents, and a charge of the reagents.

Another example method of wellbore operations is disclosed and that includes combining first and second solutions that each have a reactive monomer and a fluid that is immiscible with a fluid in the other solution, and at least one of the first or second solutions having a signaling agent, forming an emulsion with the first and second solutions that includes a continuous phase, and amounts of a dispersed phase containing the signaling agent and distributed within the continuous phase, forming polymeric layers around the amounts of the dispersed phase by reacting the monomers that define capsules containing the signaling agent, adjusting a concentration of a one of the reactive monomers to adjust a characteristic of polymer layers, disposing the capsules in cement that lines a wellbore, and evaluating a condition of the cement by sensing signaling agent that has escaped from the capsules in the cement. The step of monitoring in this example includes using colorimetric spectroscopy, infrared spectroscopy, mass spectroscopy, visual inspection, a radiation detector, and combinations thereof. Example emulsions include a water in oil emulsion, an oil in water emulsion, an oil in oil emulsion, and a water in water emulsion. The reactive monomers optionally include compounds having multi-functional reactive groups. Embodiments of the fluids include water, chloroform-cyclohexane, ethanol, and combinations thereof. Examples of the signaling agent include colored dyes, fluorophore, isotopes, fluorescent dyes, fluorescein, and combinations thereof.

A further example method of wellbore operations is described which includes using an interfacial polymerization technique of combining a monomer with a cross-linking monomer to form capsules that are made up of a signaling agent disposed within a polymer layer, adjusting an amount of the cross-linking monomer to control a characteristic of the polymer layer, disposing the capsules in a wellbore, and assessing a characteristic of the wellbore based on sensing the signaling agent escaping the capsules. In an example the capsules are disposed in wellbore cement. One example characteristic of the wellbore is integrity of cement that lines the wellbore.

BRIEF DESCRIPTION OF DRAWINGS

Some of the features and benefits of the present disclosure having been stated, others will become apparent as the description proceeds when taken in conjunction with the accompanying drawings, in which.

Figure 1:
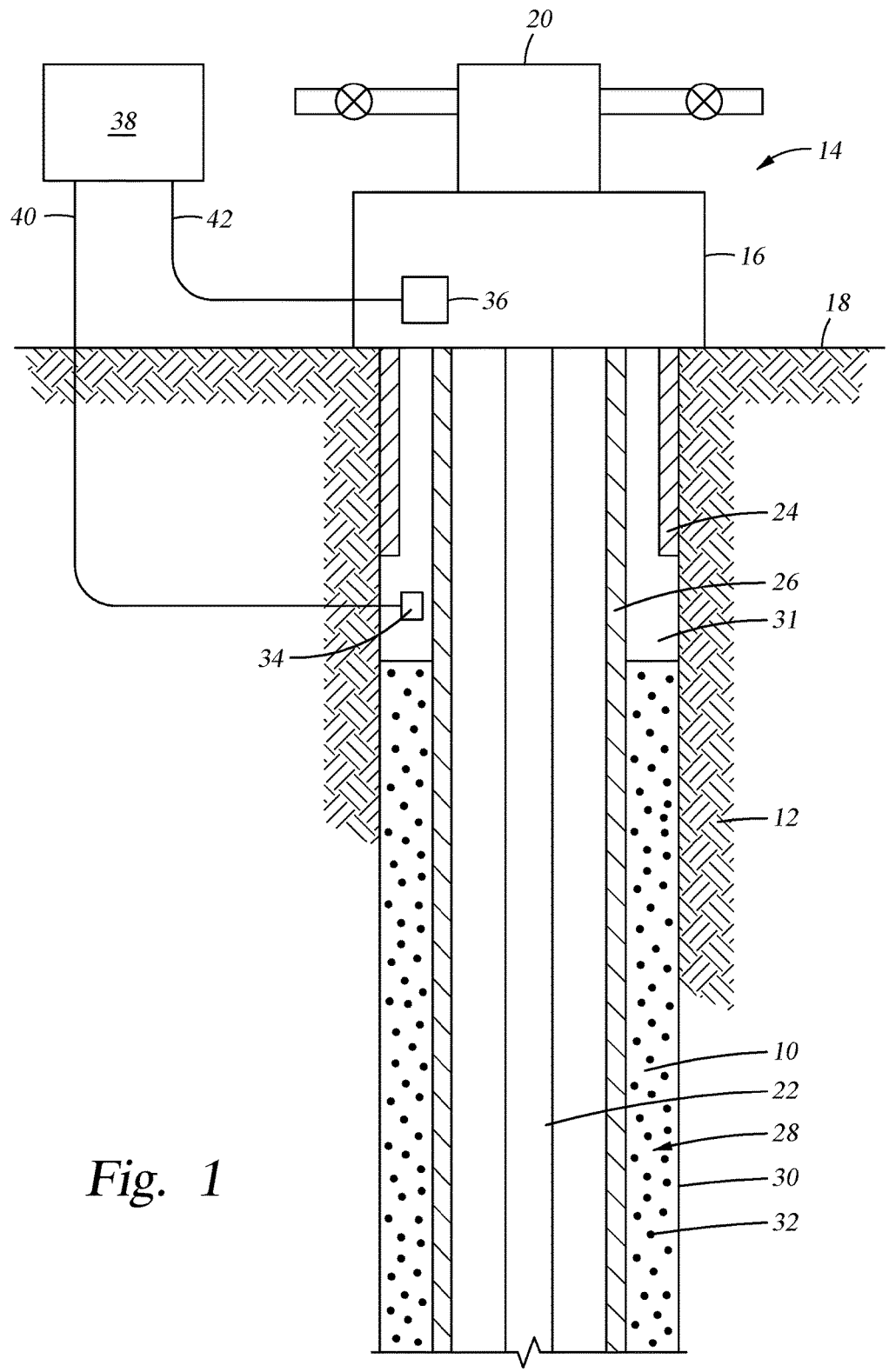
FIG. 1 is a side partial sectional view of an example of a wellbore with casing and cement, where capsules having a signaling agent are disposed in the cement.

While the advantages will be described in connection with disclosed embodiments, it will be understood that it is not intended to be limited to those embodiments. On the contrary, it is intended to cover all alternatives, modifications, and equivalents, as may be included within the spirit and scope as defined by the appended claims.

DETAILED DESCRIPTION

The method and system of the present disclosure will now be described more fully with reference to the accompanying drawings in which embodiments are shown. The method and system of the present disclosure may be in many different forms and should not be construed as limited to the illustrated embodiments set forth; rather, these embodiments are provided so that this disclosure will be thorough and complete, and will fully convey its scope to those skilled in the art. Like numbers refer to like elements throughout. In an embodiment, usage of the term "about" includes +/−5% of the cited magnitude. In an embodiment, usage of the term "substantially" includes +/−5% of the cited magnitude.

It is to be further understood that the scope of the present disclosure is not limited to the exact details of construction, operation, exact materials, or embodiments shown and described, as modifications and equivalents will be apparent to one skilled in the art. In the drawings and specification, there have been disclosed illustrative embodiments and, although specific terms are employed, they are used in a generic and descriptive sense only and not for the purpose of limitation.

Illustrated in a side partial sectional view in FIG. 1 is an example of monitoring signaling agents released from within a wellbore 10, where the wellbore 10 intersects a subterranean formation 12. Included in the embodiment depicted is a wellhead assembly 14 shown mounted over an opening of the wellbore 10, and which provides pressure control of the wellbore 10. In the illustrated example, wellhead assembly 14 includes a wellhead housing 16 which mounts on surface 18. A production tree 20 is affixed to wellhead housing 16 for selectively distributing hydrocarbons produced from formation 2. Production tubing 22 is inserted within wellbore 10, and conveys hydrocarbons to wellhead assembly 12 from the wellbore 10 produced from formation 12. A conductor pipe 24 depends from a lower end of housing 16 into wellbore 10 and intersects the opening of wellbore 10. Casing 26 is shown lining the wellbore 10, and which extends in the wellbore 10 past a terminal end of conductor pipe 24. Casing 26 is spaced radially inward from the sidewalls of wellbore 10 so that an annulus 28 is formed between the outer surface of casing 26 and sidewalls of wellbore 10. In this example, cement 30 fills a portion of annulus 28 and does not extend to the surface 18. An annular space 31 is defined within annulus 28 between surface 18 and the upper surface of cement 30.

Capsules 32, which in an example contain one or more signaling agents, are shown scattered within cement 30. In an embodiment, capsules 32 collapse or otherwise fracture when subjected to a designated pressure or temperature and release the signaling agents. Alternatives exist where signaling agents permeate from within capsules 32. Included in the present description are example methods of forming capsules 32 to collapse or fracture under designated conditions; also available are example methods of forming capsules 32 that release signaling agents through osmosis. Examples of signaling agents include a substance detectable upon irradiation of electromagnetic energy, such as but not limited to a spectrometer, a fluoroscope, ultraviolet light and the like. Example components of a signaling agent include, a solubilized oilfield chemical reagent, a dye, a colorimetric dye, a water soluble dye, and a water soluble colorimetric dye, a fluorophore, an isotope, and combinations thereof. In one embodiment, a sensor 34 is shown within annular space 31, and which can sense the presence of signaling agents released from the capsules 32. In another embodiment, sensor 36 is shown coupled with or disposed within wellhead assembly 12. Each of the sensors 34, 36 are depicted in communication with a controller 38 via respective communication means 40, 42. Example communication means 40, 42 include a hard-wired system, fiber optics, a wireless system, or combinations thereof. In the illustrated example, controller 38 receives data from sensors 34, 36 and detects or estimates the presence of a signaling agent sensed by sensors 34, 36. In an alternative embodiment, controller 38 in conjunction with one or more of sensors 34, 36, identifies a concentration, mass, or volume of the signaling agent(s).

Figure 2:
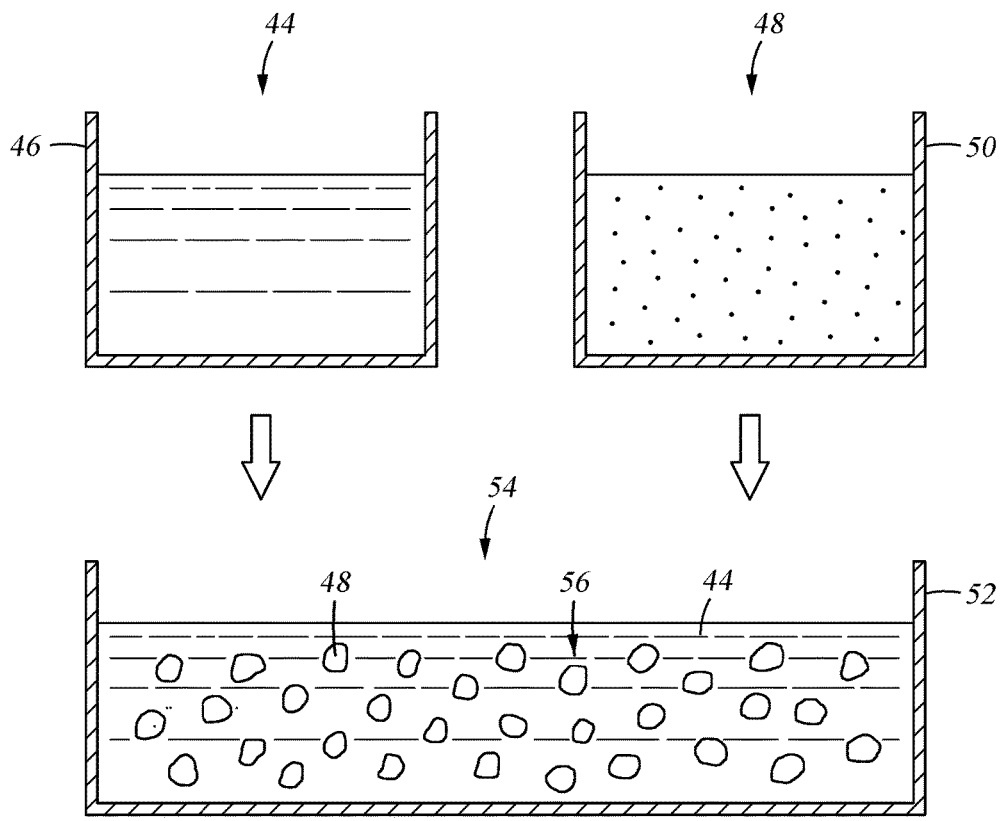
FIGS. 2 and 3 are schematic examples of forming the capsules of FIG. 1.

FIG. 2 shows in schematic form one example of a step of forming capsules 32 of FIG. 1. Here, a first fluid 44 is in a first container 46; and a second fluid 48 is shown disposed within a second container 50. In this example, the first and second fluids 44, 48 are immiscible with respect to one another; so that when first and second fluids 44, 48 are combined in a third container 52, an emulsion 54 is formed having a dispersed phase and a continuous phase. In the example of FIG. 2, amounts of the second fluid 48 are shown distributed throughout the first fluid 44 in container 52. In one embodiment, the first fluid 44 makes up a continuous phase. In another embodiment, the second fluid 48 makes up a dispersed phase. In yet another embodiment, second fluid 48 includes a signaling agent. Further in the example of forming the capsules 32, vesicles 56 are formed in the emulsion 54 which include or contain primarily the contents of the second fluid 48, and which is dispersed within first fluid 44. Examples exist where the emulsion 54 is a water and oil emulsion, an oil and water emulsion, an oil and oil emulsion, a water and water emulsion, and combinations thereof. Further in the example, the first and second fluids 44, 48 are water or oil, and where monomer reagents are dispersed into each of the fluids 44, 48.

Figure 3:
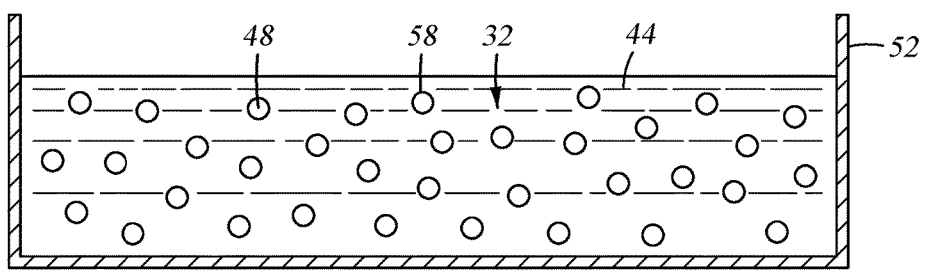

In an optional example, the fluids 44, 48 are made up of a combination of solvents and reagents. In an alternate example, the first fluid 44 contains a polar solvent, whereas the second fluid 48 contains a non-polar solvent, and optionally, first fluid 44 contains a non-polar solvent and the second fluid 48 contains a polar solvent. In an example the polar solvent includes water and the non-polar solvent includes a hydrocarbon substance such as an oil, chloroform, cyclohexane, a mix of chloroform and cyclohexane, and including combinations. In the example of FIGS. 2 and 3 the signaling agent is included within the second fluid 48.

Shown in a side sectional view in FIG. 3 is a schematic example of capsules 32 forming within the container 52, where polymer membranes 58 define an outer layer of the capsules 32, and in which the capsules 32 have an amount of second fluid 48 captured within the polymer membranes 58. In an embodiment, each of the first and second fluids 44, 48 contain separate reagents that when combined form the polymer membrane 58, and which encapsulates the vesicles 56 of FIG. 2. Further in the example illustrated in FIG. 3, the irregularly shaped vesicles 56 of FIG. 2, become spherically shaped capsules 32 as shown in FIG. 3. Embodiments exist where diameters of the capsules 32 range in magnitude from about 10 microns to about 50 microns. Examples of the different reagents that may be included in the first and second fluids 44, 48 include monomers with multiple functional reactive groups, such as acid chlorides that react with monomers having di-functional amino groups that form amide bonds. In an embodiment, the monomers include aromatic compounds having multi-functional reactive groups.

Optionally, the multifunctional monomers form polyamide and polyaramide membranes that form a polyamide shell making up the polymer membrane 58. Shown in Table 1 are example reactions for forming the polymer membrane 58.

TABLE 1

| Monomer A | Monomer B | Crosslinked polymer |
|---|---|---|
| 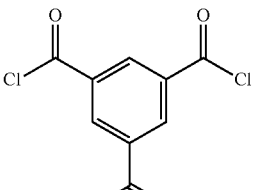 (1) | 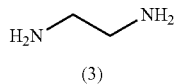 (3) | 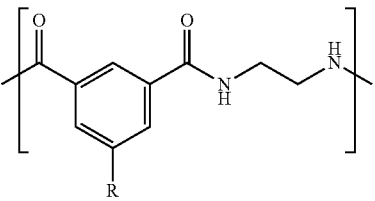 (7) |
| 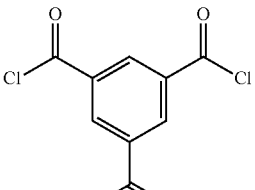 (1) | 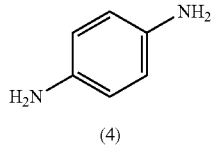 (4) | 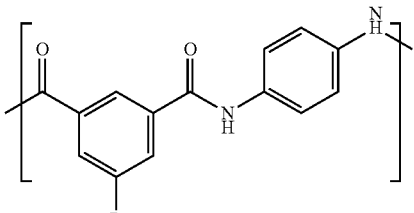 (8) |
| 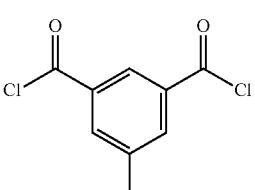 (1) | 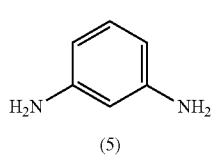 (5) | 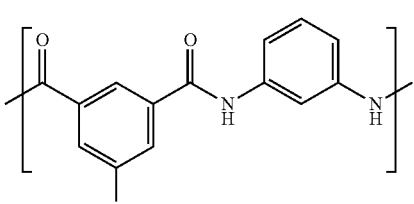 (9) |
| 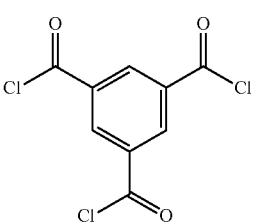 (1) | 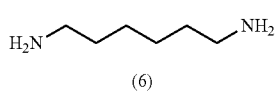 (6) | 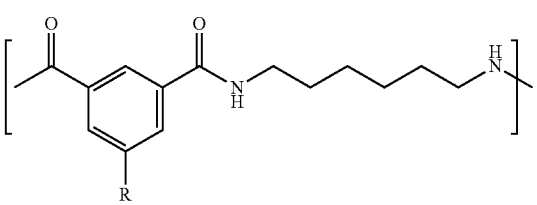 (10) |

TABLE 1-continued

| Monomer A | Monomer B | Crosslinked polymer |
|---|---|---|
| 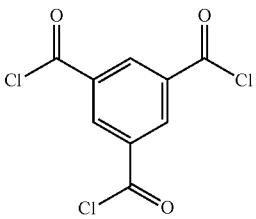 (1) | 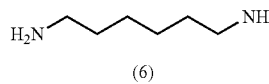 (6) | 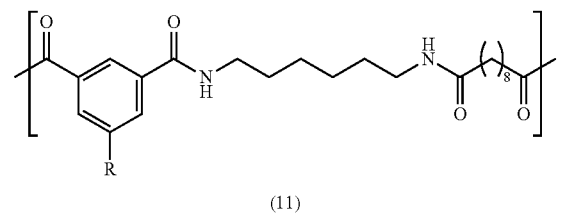 (11) |
| 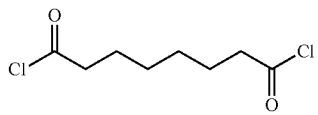 (2) | | |

Reference numerals are assigned to the chemical compounds provided in Table 1 and where the names of the chemicals with the assigned reference numerals are: (1) 1,3,5-benzenetricarboxylic acid chloride; (2) sebacoyl chloride; (3) ethylenediamine; (4) 1,4-diaminobenzene; (5) 1,3-diaminobenzene; (6) 1,6-diaminohexane; (7) poly(ethylene trimesoylamide); (8) poly-(para-phenylene trimesoylamide); (9) poly-(meta-phenylene trimesoylamide); (10) poly(hexamethylene trimesoylamide); and (11) poly(hexamethylene-co-sebacoyl trimesoylamide).

In the example of Table 1, the reactive monomers are classified as Monomer A, Monomer B, and Co-monomer A. Monomer A is depicted as 1,3,5-benzenetricarboxylic acid chloride, but can be any compound having multi-functional reactive groups, and being the range of $C_8$-$C_{12}$ or more. In an alternative, Monomer A can be aromatic, cyclic, or linear. Examples of Monomer B provided in Table 1 are compounds with di-functional amide groups, where the compounds include aromatic and linear organic compounds. In an alternative, Monomer B includes cyclic organic compounds with multi-functional amide or amine groups. Example compounds making up Monomer B range from $C_2$-$C_8$ or more. In an alternate embodiment, a Co-monomer A is used in conjunction with Monomer A, and which is shown in Table 1 as sebacoyl chloride. Alternatively, Co-monomer A includes a cyclic or aromatic compound with multiple function reactive groups. In one non-limiting example, Monomer A and Monomer B are disposed in separate ones of the first and second fluids 44, 48 prior those fluids 44, 48 being combined. Embodiments exist where Co-monomer A is included in the same fluid as Monomer A. Example polymerization times range from about 8 hours, about 24 hours, and greater than 24 hours.

In one example, the compound having the tri-functional reactive acid chlorides is referred to as a cross-linker. In an alternative, the cross-linker defines a reagent or compound having more functional reactive groups than another reagent or compound being reacted with the cross-linker to form a polymer. Not intending to be bound by theory, but it is believed that varying the concentrations of the cross-linker adjusts the permeability and strength of the polymer membrane 58. In an alternative, the release rate of the signaling agent is controlled by: (1) changing the viscosity of the dispersed phase within the emulsion 54; (2) the permeability of the polymer membrane 58, (3) the size and charge of the reagents used to form the polymer membrane 58; or (4) selective combinations of these. In other alternatives, the size, shape, or both the size and shape of the vesicles 56 is controlled by altering a mixing speed used for combining the first and second fluids 44, 48 within the container 52. In an example, a laminar flow is generated during interfacial polymerization and hollow fibers (not shown) are formed. Optionally, additional materials are encapsulated within the polymer membrane 58, and which in an alternative include sealing reagents, such as polymer, salt, rubber, water or any other chemistries needed to self-seal fractured cement. Additional additives within the polymer membrane 58 include cement additives, gas scrubbers, and anti-gas migration additives.

In an embodiment, integrity of the cement 30 of FIG. 1 is selectively monitored over the life of the well by formulating the polymer membrane 58 to collapse or otherwise rupture under a designated pressure or temperature. In an illustrative example, when the sensors 34, 36 sense signaling agents that have been released from capsules 32 that rupture in response to exposure to a designated pressure or temperature, an indication of conditions of the cement 30 is obtainable. In one example, the capsules 32 rupture in response to a combination of a designated temperature and pressure. In an alternative, sensing signaling agents with sensors 34, 36, that was released from ruptured capsules 32 disposed in the cement 30, is an indicator of possible failure of the cement 30. One example of a designated pressure occurs in the cement 30 from gas migrating into the cement 30 from the adjacent formation 12. Thus examples exist where the presence of micro-annuli in the cement 30 is detected by implementing the described method. In a further optional step, capsules 32 that burst or rupture at different ambient pressures or temperatures, are disposed at different depths within the wellbore 10, so that specific conditions at designated depths are detectable. In an optional alternative, capsules 32 disposed at different depths contain different signaling agents. Thus by sensing a particular signaling agent with sensors 34, 36, knowledge of a particular condition occurring at a particular depth is obtainable, and which is optionally registered within controller 38.

Example

Figure 4:
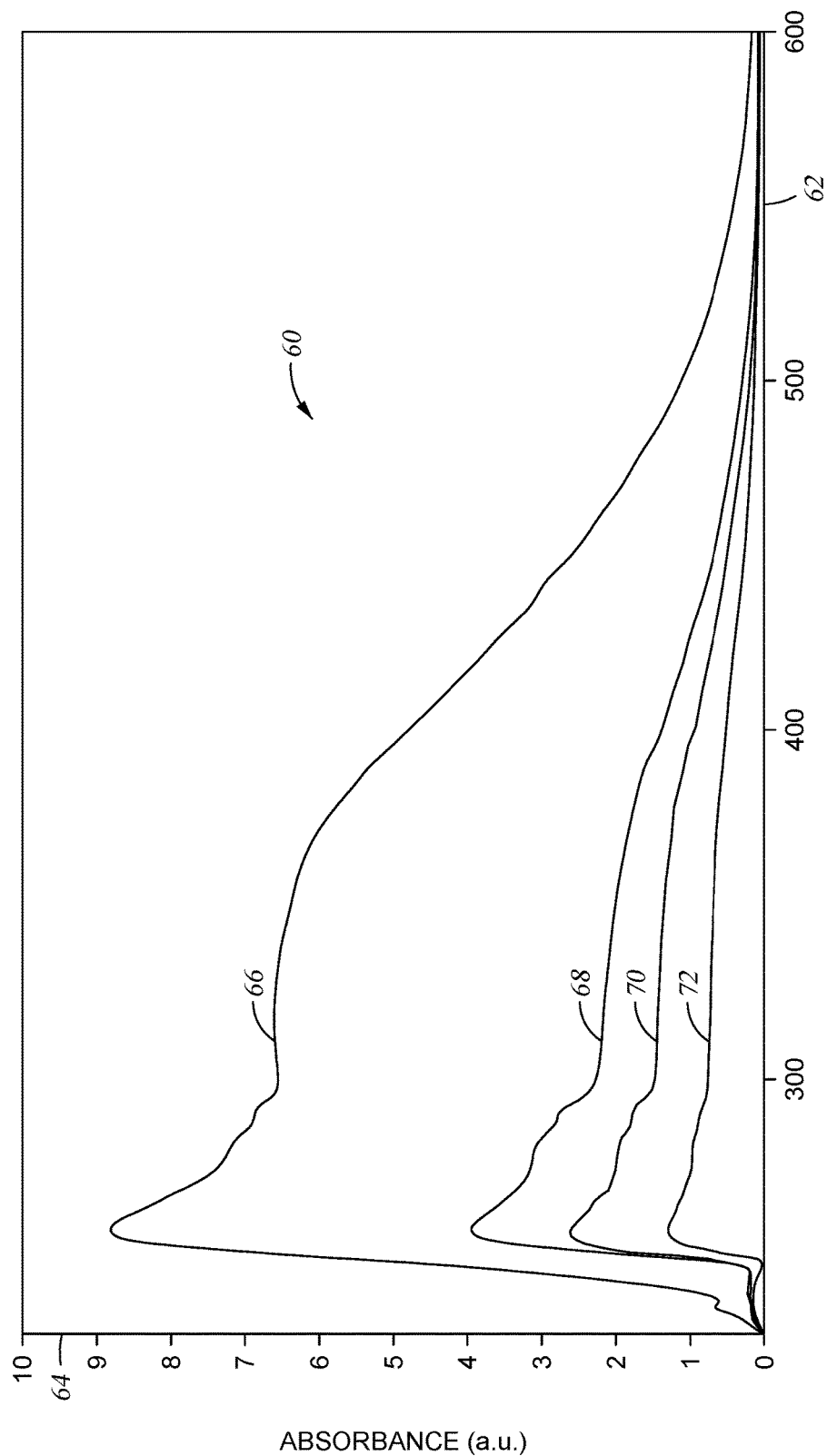
FIG. 4 is a graph having example plots representing light absorbance versus wavelength of capsules with membranes formed to have different characteristics.

In one non-limiting example, groups of capsules 32, with encapsulated colorimetric dye SAFC, were vacuum filtered and dried into a free flowing powder. An amount of 20 ml of basic water (pH=9) was separately combined with 0.2 g of each group of capsules 32. In each sample of water and the group of capsules 32, the dye in the capsules 32 permeated through the membranes 58 and tinted the water with the color of the dye. Absorbance values for each sample of the tinted water were measured with a spectrometer. The measured absorbance values provided correlations to permeability of the membranes 58 of each group of capsules 32. The polymer membranes 58 of each group of capsules 32 were formed having a different amount of a cross-linker. Not intending to be bound by theory, it is believed that the permeability of the membranes 58, and thus the measured absorbance values, were directly affected by the amount of cross-linker added during the process of forming the capsules 32. Referring now to FIG. 4, shown is a graph 60 with an X-Y axis having an abscissa 62 and an ordinate 64. Charted on graph 60 are a series of plots 66, 68, 70, 72 that graphically illustrate results of this example of illuminating different groups of capsules 32, and measuring an absorbance of that light for each group of capsules 32. In FIG. 4, abscissa 62 represents the wavelength of a light being emitted into the tinted water, and corresponding light absorbance of the tinted water is presented along the ordinate 64. The different plots 66, 68, 70, 72 each represent measured absorbance values over a range of wavelengths of illuminated light, of water tinted by the different groups of capsules 32 made from different amounts of a cross-linker. More specifically, plot 66 represents absorbance data obtained from 2 ml of water tinted by the addition of a group of capsules 32 whose corresponding polymer membranes 58 were formed with a cross-linker having a concentration of 23.1 millimolar. Plot 68 represents the absorbance obtained from water tinted from 2 ml of water tinted by a group of capsules 32 where the cross-linker concentration was 46.2 millimolar, in plot 70 the cross-linker concentration when forming the group of capsules 32 was 76.9 millimolar, and in plot 72 the cross-linker concentration when forming the group of capsules 32 was 153.8 millimolar. As illustrated in the example of FIG. 4, it can be observed at the intensity of the absorbance (as illustrated by the values taken along the ordinate 64) increases with a decrease in the corresponding cross-linker concentration within the capsules 32. As such, the permeability of the polymer membrane 58 making up the individual capsules 32 decreases with an increase in the cross-linker concentration. Accordingly, examples exist where the yield strength or tensile strength of the capsule 32 is increased by increasing cross-linker concentration when forming the polymer membrane 58. In examples, the release rate of signaling agent from the capsules 32 varies with permeability of the membranes 58 of the capsules 32. Because concentrations of cross-linkers added to form the membranes 58 affects the permeability of the membranes 58 (and thus the capsules 32), embodiments exist where a designated release rate is obtained with strategic control of cross-linker concentrations. In a non-limiting example, a release rate of the signaling agent from the polymer membranes 58 is controlled by adjusting one or more of, a viscosity of the fluids 44, 48, a permeability of the polymer membranes 58, a size of the reagents, and a charge of the reagents. It is within the capabilities of those skilled in the art to identify and/or add particular amounts of cross-linking constituents when forming the capsules 32, so that the polymer membranes 58 of the capsules 32 have a designated yield strength to yield, rupture, or burst under certain environmental conditions such as pressure, temperature, or a combination of both. It is further within the capabilities of those skilled in the art to identify and/or add particular amounts of cross-linking constituents when forming the capsules 32, so that the polymer membranes 58 of the capsules 32 have a designated permeability.

Embodiments of controlling permeability of membranes 58 include using different starting diamine monomers (hexadiamine vs. phenylenediamine, for example). Optionally, strength of a membrane 58 is obtained by allowing increased reaction time to polymerize to a greater molecular weight, which in one example is a minimum of six hours. In an embodiment, hexadiamene monomer is included when forming the capsules 32, which provides high permeability and high strength.

In an example, a designated permeability of a polymer membrane 58 with a capsule 32 depends on a size of molecules within the signaling agent. In this example, for capsules 32 having signaling agents with different sized molecules, and that have substantially the same release rate, the capsules 32 containing the signaling agent of a higher molecular weight would be formed with a polymer membrane 58 having a higher permeability (i.e. lower cross-linker concentration).

Figure 5:
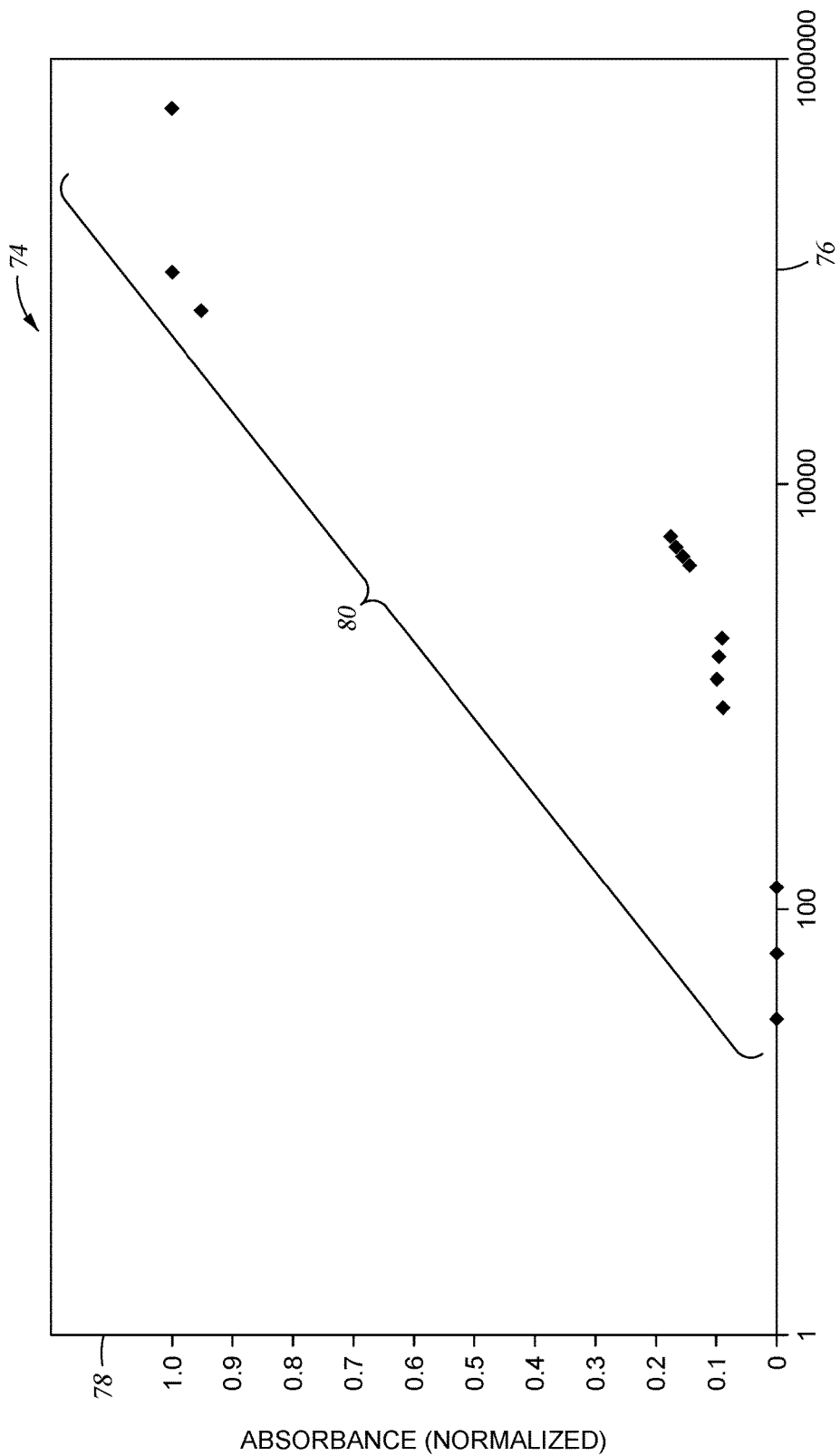
FIG. 5 is a graph with examples of absorbance over time of material being sensed that was released from the capsules of FIG. 1.

FIG. 5 shows a graph 74 having an X-Y axis, and with an abscissa 76 and ordinate 78. Represented in FIG. 5 is a prophetic example of monitoring events downhole is illustrated where the signaling agent is detected spectroscopically to obtain values of absorbance; and values of measured absorbance over time are plotted. Values of time in FIG. 5 are represented along the abscissa 76, and values of absorbance are represented by ordinate 78. Data points 80 represent instances of dye being detected by one or more sensors 34, 36 (FIG. 1), where the dye had been released from the capsules 32 disposed in cement 30. This illustrates a measure of the signaling agent monitored over time, and as time increases so does the normalized value of the absorbance. A triggered release shows a delay in detection. Over time, the release rate of the encapsulated signaling agent into solution is detected and increases until spent. The data illustrates a passive release.

Advantages of disclosed embodiments include a one-pot synthesis of forming the capsules 32. Alternate embodiments provide an advantage of encapsulating different signal chemical additives, polymers, and dispersed solutions with a robust capsule 32 for embedment into cement 30. Further advantages include that loading amounts of signaling agents in the hollow shells are optionally changed, polymer shell shields signaling agents from environment, shell is elastic, embodiments of polymer layers are heat resistant and useful in high temperature applications, cement properties are improved with release of optional additives in capsules, and pressure excursions that exceed a designated amount are detectable with the release of encapsulated signaling agents.

The present improvement described is well adapted to carry out the objects and attain the ends and advantages mentioned, as well as others that are inherent. While embodiments of the present description have been given for purposes of disclosure, numerous changes exist in the details of procedures for accomplishing the desired results. In an example, capsules 32 can remain intact within the cement 30 and not rupture. The intact capsules 32 can optionally affect mechanical properties of the cement 30, such as by increasing or decreasing ductility, flexibility, tensile strength, or yield strength of the cement 30. These and other similar modifications will readily suggest themselves to those skilled in the art, and are intended to be encompassed within the spirit of the present disclosure and the scope of the appended claims.

What is claimed is:

1. A method of wellbore operations comprising:
providing a first fluid having a signaling agent and a first reagent;
providing a second fluid that is immiscible with the first fluid and that contains a second reagent that is combinable with the first reagent to form a polymer;
combining the first and second fluids so that the first fluid is dispersed in the second fluid to form vesicles of the first fluid in the second fluid, and so that the first and second reagents react at interfaces between the first and second fluids to form polymer layers that encapsulate the vesicles, and which form capsules containing the signaling agent;
controlling a characteristic of the polymer layers by adjusting a concentration of a one of the first and second reagents;
disposing the capsules in a wellbore; and
monitoring for the presence of signaling agents that escape from the capsules.

2. The method of claim 1, where the capsules are disposed in cement in the wellbore.

3. The method of claim 1, further comprising monitoring the concentration of the signaling agent that releases from the capsules.

4. The method of claim 2, where the signaling agent comprises a first signaling agent, the method comprising forming capsules having a second signaling agent and disposing the capsules having the second signaling agent at a designated depth in the wellbore that is different from a depth where capsules having the first signaling agent are disposed in the wellbore.

5. The method of claim 2, further comprising identifying a characteristic of the cement based on the step of monitoring the signaling agent.

6. The method of claim 1, where the signaling agent comprises a material selected from the group consisting of a dye, a fluorophore, an isotope, and combinations thereof.

7. The method of claim 1, where the first and second reagents comprise compounds having a reactive functional group and are selected from the group consisting of monomers with tri-functional acid chlorides and monomers with di-functional amino groups.

8. The method of claim 1, further comprising encapsulating a sealing reagent for sealing cement.

9. The method of claim 1, where the characteristics of the polymer layers comprise permeability and yield strength.

10. The method of claim 1, where the polymer layers are formulated to fail at one of a designated pressure, a designated temperature, or a designated temperature and designated pressure.

11. The method of claim 1, further comprising controlling a release rate of the signaling agent from the polymer layers by adjusting one or more of, a viscosity of the first fluid, a permeability of the polymer layers, a size of the reagents, and a charge of the reagents.

12. A method of wellbore operations comprising:
combining first and second solutions that each comprise a reactive monomer and a fluid that is immiscible with a fluid in the other solution, and at least one of the first or second solutions having a signaling agent;
forming an emulsion with the first and second solutions that comprises a continuous phase, and amounts of a dispersed phase containing the signaling agent and distributed within the continuous phase;
forming polymeric layers around the amounts of the dispersed phase by reacting monomers that define capsules containing the signaling agent;
adjusting a concentration of a one of the reactive monomers to adjust a characteristic of polymer layers;
disposing the capsules in, cement that lines a wellbore; and
evaluating a condition of the cement by sensing signaling agent that has escaped from the capsules in the cement.

13. The method of claim 12, where the step of evaluating comprises using colorimetric spectroscopy, infrared spectroscopy, mass spectroscopy, visual inspection, a radiation detector, and combinations thereof.

14. The method of claim 12, where the emulsion is selected from a group comprising a water in oil emulsion, an oil in water emulsion, an oil in oil emulsion, and a water in water emulsion.

15. The method of claim 12, where the reactive monomers comprise compounds having multi-functional reactive groups.

16. The method of claim 12, where the fluids are selected from the group consisting of water, chloroform-cyclohexane, ethanol, and combinations thereof.

17. The method of claim 12, where the signaling agent is selected from the group consisting of colored dyes, fluorophore, isotopes, fluorescent dyes, fluorescein, and combinations thereof.

18. A method of wellbore operations comprising:
using an interfacial polymerization technique that comprises combining a monomer with a cross-linking monomer to form capsules that comprise a signaling agent disposed within a polymer layer;
adjusting an amount of the cross-linking monomer to control a characteristic of the polymer layer;
disposing the capsules in a wellbore; and
assessing a characteristic of the wellbore based on sensing the signaling agent escaping the capsules.

19. The method of claim 18, where the capsules are disposed in wellbore cement.

20. The method of claim 18, where the characteristic of the wellbore comprises integrity of cement that lines the wellbore.

* * * * *